United States Patent [19]

Benoit et al.

[11] Patent Number: 5,182,295
[45] Date of Patent: Jan. 26, 1993

[54] INSECTICIDAL BENZOFURAN DERIVATIVES

[75] Inventors: Marc Benoit, Roquevaire; Jean-Louis Brayer, Nanteuil le Haudouin; Jean-Pierre Demoute, Neuilly Plaisance; Gilles Mourioux, Gemenos; Laurent Taliani, Les Pavillons sous Bois, all of France

[73] Assignee: Roussel Uclaf, Paris, France

[21] Appl. No.: 770,986

[22] Filed: Oct. 1, 1991

[30] Foreign Application Priority Data

Oct. 2, 1990 [FR] France ................ 90 12103

[51] Int. Cl.$^5$ .................. A61K 31/34; A61K 31/425; C07D 307/79; C07D 277/24
[52] U.S. Cl. .................... 514/365; 514/464; 514/469; 548/204; 549/435; 549/468; 549/469; 549/471
[58] Field of Search .............. 549/435, 468, 469, 471; 548/204; 514/365, 464

[56] References Cited

U.S. PATENT DOCUMENTS 4,143,154  3/1979  Scherrer et al. ............ 549/464
4,863,503  9/1989  Anthony et al. ............ 514/438

Primary Examiner—Bernard Dentz
Attorney, Agent, or Firm—Bierman and Muserlian

[57] ABSTRACT

A compound of the formula

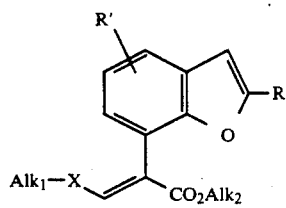

wherein R is selected from the group consisting of hydrogen, optionally substituted alkyl, alkenyl and alkynyl of up to 8 carbon atoms, optionally substituted cycloalkyl or cycloalkenyl of up to 8 carbon atoms, optionally substituted aryl of 6 to 18 carbon atoms, optionally substituted aralkyl of 7 to 24 carbon atoms, optionally substituted benzoyl and optionally substituted heterocycle, the optional substituents being at least one member of the group consisting of halogen, phenoxy, thiazolyl, alkyl and alkoxy of 1 to 6 carbon atoms and haloalkyl, $Alk_1$ and $Alk_2$ are individually optionally substituted alkyl of 1 to 8 carbon atoms, X is —O— or —S— and R' is hydrogen or halogen in any position on the phenyl and the geometry of the double bond is E or Z or a mixture of E and Z and having useful pesticidal properties.

23 Claims, No Drawings

INSECTICIDAL BENZOFURAN DERIVATIVES

STATE OF THE ART

Related prior art includes U.S. Pat. No. 4,863,503 and U.S. Pat. No. 4,143,154.

OBJECTS OF THE INVENTION

It is an object of the invention to provide the novel benzofurans of formula I and a novel process for their preparation.

It is another object of the invention to provide novel pesticidal composition and a novel method of combatting pests.

These and other objects and advantages of the invention will become obvious from the following detailed description.

THE INVENTION

The novel benzofurans of the invention have the formula

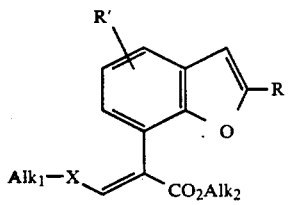

wherein R is selected from the group consisting of hydrogen, optionally substituted alkyl, alkenyl and alkynyl of up to 8 carbon atoms, optionally substituted cycloalkyl or cycloalkenyl of up to 8 carbon atoms, optionally substituted aryl of 6 to 18 carbon atoms, optionally subtituted aralkyl of 7 to 24 carbon atoms, optionally substituted benzoyl and optionally substituted heterocycle, the optional substituents being at least one member of the group consisting of halogen, phenoxy, thiazolyl, alkyl and alkoxy of 1 to 6 carbon atoms and haloalkyl, $Alk_1$ and $Alk_2$ are individually optionally substituted alkyl of 1 to 8 carbon atoms, X is —O— or —S— and R' is hydrogen or halogen in any position on the phenyl and the geometry of the double bond is E or Z or a mixture of E and Z.

When R is alkyl, it is preferably methyl, ethyl, propyl, isopropyl, butyl, isobutyl, sec-butyl, tert-butyl, pentyl or hexyl. When R is alkenyl, it is preferably vinyl or 1,1-dimethyl allyl and when R is alkynyl, it is preferably ethynyl or propynyl.

When R is cycloalkyl, it is preferably cyclohexyl and when R is cycloalkenyl, it is preferably cyclohexenyl. When R is substituted alkyl, alkenyl, alkynyl, cycloalkyl or cycloalkenyl, it is preferably alkyl, alkenyl or alkynyl substituted by one or more halogens, for example —$CH_2F$, —$CHF_2$, —$CF_3$, —$CCl_3$ or —$CBr_3$.

When R is aryl, it is preferably phenyl, biphenyl or naphtyl. When R is arylalkyl, it is preferably benzyl optionally substituted on the methylene by hydroxy or hydroxyimino.

When R is heterocyclic, it is preferably a heterocyclic containing 1 or more nitrogen, oxygen or sulfur atoms. Examples are thienyl, furyl, pyrrolyl, imidazolyl, pyrazolyl, pyridyl, pyrazinyl, pyrimidinyl, pyridazinyl, oxazolyl, isothiazolyl, isoxazolyl, thiazolyl, oxadiazolyl and thiadiazolyl.

When R is substituted aryl, arylalkyl, benzoyl or heterocyclic, the substituents is preferably chosen from the group constituted by halogen, alkyl of 1 to 8 carbon atoms, —$CF_3$, —$CH_2F$, —$CHF_2$, —CN, —$NO_2$, alkoxycarbonyl, —$CONH_2$, —$OCF_3$, optionally substituted phenyl or phenoxy, alkylamino or dialkylamino of 1 to 4 carbon atoms. It can consist of two substituents carried by 2 adjacent carbon atoms forming an alkylenedioxy, or of one or more substituents, —OR", —SR" in which R" is alkyl or alkenyl of 1 to 6 carbon atoms, or heterocyclic such as thienyl, furyl thiazolyl, oxazolyl, pyridinyl, pyrazinyl, pyrimidinyl, isoxazolyl, isothiazolyl, oxadiazolyl, or thiadiazolyl as defined above.

By alkylamino or dialkylamino, it is meant methylamino, ethylamino, dimethylamino, diethylamino and methylethylamino.

Among the preferred compounds of formula I are those wherein X is oxygen, those wherein R' is hydrogen, those wherein $Alk_1$ and $Alk_2$ are methyl, those wherein R is alkyl of 1 to 8 carbon atoms, preferably n-butyl, those wherein R is phenyl optionally substituted with at least one member of the group consisting of halogen, preferably chlorine or bromine, alkoxy of 1 to 6 carbon atoms, preferably 1 to 4 carbon atoms, phenoxy, thiazolyl and alkyl with at least one halogen such as —$CF_3$ and phenyl with alkylenedioxy on two adjacent carbon atoms and those wherein R is thiazolyl optionally substituted with alkyl of 1 to 8, preferably 1 to 4 carbon atoms, especially isopropyl and those wherein R is optionally substituted phenyl such as trifluoromethoxyphenyl.

Preferably, the enol ether double bond is of E geometry. The preferred compounds of the invention are those of Examples 1, 3, 11, 14, 15, 16, 17, 18, 19 and 28.

The novel process of the invention for the preparation of a compound of formula I comprises reacting a compound of the formula

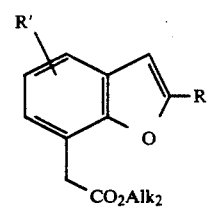

wherein R, R' and $Alk_2$ have the above definition with a formylation agent to obtain a compound of the formula

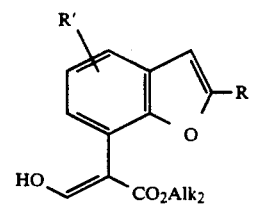

reacting the latter with an alkylation agent to obtain a compound of the formula

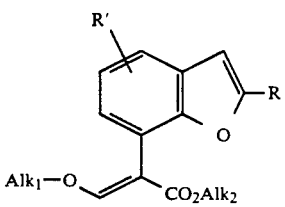

in which $Alk_1$ has the above definition, optionally reacting the latter with an agent capable of replacing the oxygen with a sulfur to obtain a compound of the formula

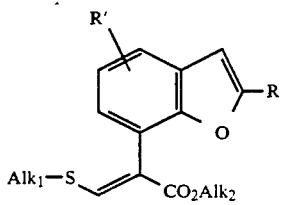

The formylation reaction can be carried out with a strong base such as sodium hydride in an appropriate solvent followed by the action of an alkyl formate, preferably methyl, or by the action of dimethylformamide acetals followed by hyrolysis in an acid medium, or also by the action of a strong base such as lithium diisopropyl amide followed by the action of a trialkylsilyl halide, the silylated enol ether thus formed being then subjected to the action of a trialkyl orthoformate in the presence of titanium tetrachloride.

The alkylation reaction takes place using an alcohol under standard conditions or an alkyl iodide on the enolate formed intermediately by the action of sodium hydride on compound III, or also an alkyl iodide in the presence of potassium carbonate in acetone. The oxygen-sulfur exchange reaction is carried out using an alkyl thiolate.

The compounds of formulae II and III are new products and are in themselves a subject of the present invention. The preferred compounds of formulae II and III are those described in the examples, especially Examples 1, 2, 11, 12, 14, 15, 16, 17, 18, 19 and 28.

The compounds of formulae II and III can be prepared by the following methods:

a)

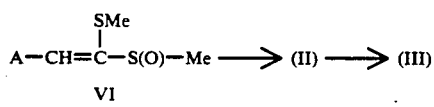

b)

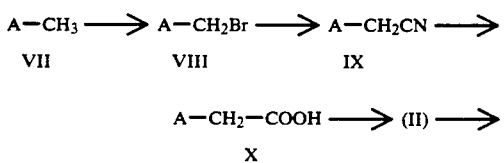

A is or also, when R is optionally substituted thiazolyl, by the following method:

c)

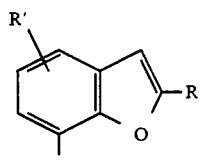

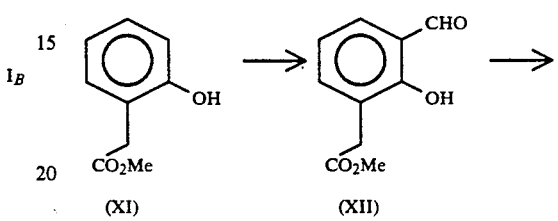

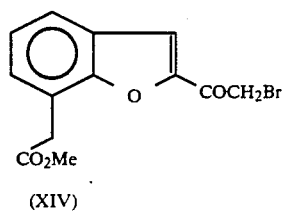

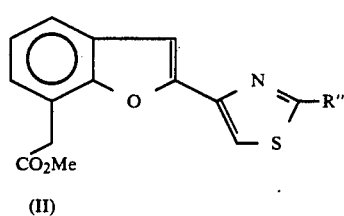

The compounds of formulae IV, V, VII, XII and XIV are obtained by methods described in the literature or in preparations 1 to 4 and 14 to 19 described further on (see CASTRO et al., Journal of Organic Chemistry (1966), Vol. 31, p. 4071 to 4078; COX et al, Tetrahedron (1975) Vol. 31, p. 633; Pesticide Science (980) Vol. 11, p. 526 to 532; ROCHE et al, C.R. Acad. Scien. paris C279 (1974) p. 663 to 666; Helvetica Acta (1974), Vol. 57, (5) p. 1381; Reimer et al, Chem. Rev. Vol. 60, p. 169 to 184 (1960); Corria et al, Synthesis (1976), p. 194 to 195).

The novel pesticidal compositions of the invention are comprised of a pesticidally effective amount of at least one compound of formula I and an inert carrier. The compositions are useful to combat soil parasites, plant parasites, premise parasites and parasites of warm-blooded animals.

The compositions have useful fungicide properties which can be used for protection vis-a-vis pathogenic fungi. It can be used for the protection of plants, premises or animals. These properties can also be used in human and animal hygiene and medicine.

The compositions are useful for combatting numerous phytopathogenic fungi, especially Erysiphe graminis, Sphaerotheca *macularis, Sphaerotheca fuliginea,* Podosphaera leucotricha, Uncinula necator, Helminthosporium spp., Rhynchosporium spp., Septoria spp., *Pseudocercosporella herpotrichoides* and *Gaeumannomyces graminis,* Ustilago spp., *Cercospora arachidicola* and *Cercosporidium personatum,* Cercospora species, *Botrytis cinerea,* Alternaria spp., *Venturia inaequalis, Plasmopara viticola, Bremia lactucae,* Peronospora spp., *Pseudoperonospora humuli, Pseudopero-nospora cubensis,* Phytophthora spp. infestans, Phytophtora spp., *Puccinia recondita, Thanatephorus cucumeris,* Rhizoctonia spp. and also of fungi or yeasts relating to human health such as Candida albicans or Trychophyton spp.

The compositions of the invention are also useful as insecticides, acaricides and nematicides. They can be used notably to combat insects in the agricultural domain, to combat, for example, fleas, larvae of lepidoptera and coleoptera.

The compositions can also be used to combat insects in premises, to combat notably flies, mosquitoes and cockroaches and can also be used to combat parasitic acarida and nematodes of plants, to combat parasitic acarida of animals, to combat for example ticks and notably ticks of the Boophilus species, those of the Hyalomnia species, those of the Amblyomnia species and those of the Rhipicephalus species, or to combat all types of mites and notably the sarcoptic, psoroptic and chorioptic mite.

Preferred compositions are insecticidal compositions containing as active ingredient at least one of the products defined above.

These compositions are prepared according to the usual processes of the agrochemical or veterinary industry and can be in the form of powders, granules, suspensions, emulsions, solutions, aerosol solutions, baits or other preparations usually employed for the use of these types of compound.

Besides the active ingredient, these compositions contain generally a non-ionic surface-active vehicle and/or agent to provide a uniform dispersion of the constitutive substances of the mixture. The vehicle can be a liquid such as water, alcohol, hydrocarbons or other organic solvents, a mineral, animal or vegetable oil, a powder such as talc, clays, silicates, kieselguhr.

The insecticide compositions of the invention, as well as the acaricide and nematicide compositions, can optionally have added to them one or several other pesticide agents. The acaricide and nematicide compositions can appear notably in the form of powders, granules, suspensions, emulsions, solutions.

For acaricide use, wettable powders are preferably used for foliar spraying containing 1 to 80% of active product, or liquids for foliar spraying containing 1 to 500 g/l. of active ingredient. Powders for foliar dusting can also be used. For nematicide use, liquids ar preferably used for soil treatment containing 300 to 500 g/l. of active ingredient.

In the following examples, there are described several preferred embodiments to illustrate the invention. However, it is to b understood that the invention is not intended to be limited to the specific embodiments.

EXAMPLE 1

Methyl α-(E)-methoxymethylene1-2-(4-methoxy-phenyl)-7-benzofuranacetat and the corresponding Z isomer

STEP A: Methyl α-(E+Z)-hydroxymethylene1-2-(4-methoxy-phenyl)-7-benzofuranacetate A solution of 3 g of the product of preparation 1, 14 ml of methyl formate and 35 ml of dimethylformamide were introduced dropwise at ambient temperature into a suspension of 1 g of sodium hydride (50% in oil) in 20 ml of dimethylformamide and the mixture was stirred for 16 hours at ambient temperature, then was poured into a normal solution of hydrochloric acid. The pH of the medium was acidic and extraction was carried out with ethyl acetate. After drying and concentrating, the desired product was obtained which was used as is for the following step.

STEP B: Methyl α-[(E)-methoxymethylene]-2-(4-methoxy-phenyl)-7-benzofuranacetate and the corresponding (Z) isomer 0.5 g of sodium hydride at 50% in oil were introduced into 20 ml of dimethylformamide and a solution of 12.3 g of methyl α-[(E+Z)-hydroxymethylene]-2-phenyl-7-benzofuranacetate dimethylformamide was added dropwise. The reaction mixture was stirred for 20 minutes and 6.4 ml of methyl iodide were added all at once. The reaction mixture was stirred overnight at ambient temperature and the solution was poured into water. Extraction was carried out with ether and the extracts were dried and evaporated to dryness to obtain 6.2 g of product which was chromatographed on silica. Elution with a mixture of hexane and ethyl acetate (8-2) yielded 2 g of isomer E of the desired product melting at 176° C., and 0.3 g of isomer Z of the desired product melting at 124° C.

PREPARATION 1

Methyl 2-(4-methoxy-phenyl)-7-benzofuranacetate

STEP A: (2-bromo phenoxy)-4'-methoxy acetophenone 44.3 g of potassium carbonate were added to a mixture of 34 ml of 2-bromo phenol, 150 ml of acetone and 75 g of 4'-methoxy-2-bromo acetophenone in 150 ml of acetone. The mixture was refluxed for 16 hours and the solution was poured into water. The aqueous phase was extracted with ethyl acetate, dried, filtered and brought to dryness to obtain 101 g of the desired product melting at 104° C.

STEP B: 7-bromo-2-(4-methoxy-phenyl)-benzofuran

A mixture of 101 g of the product of Step A and 650 ml of polyphosphoric acid was heated to 160° C. for one hour and then allowed to return to ambient temperature. The mixture was poured over ice and extracted with ethyl acetate. The extracts were washed, decanted, dried and brought to dryness to obtain 82.8 g of product which was purified by chromatography on silica (eluant: hexane-isopropyl ether (98-2)). The product, not soluble in the eluant, was dissolved in ethyl acetate to obtain 36.4 g of the desired product.

STEP C:
2-(4-methoxy-phenyl)-7-benzofurancarbaldehyde 83 ml of butyllithium were added at −70° C. to a mixture of 36.4 g of the product of Step B and 100 ml of tetrahydrofuran and the mixture was stirred for one hour at −60° C., 24.2 ml of N-formyl morpholine in 50 ml of tetrahydrofuran were added and the reaction mixture was stirred for 16 hours at −60° C. Ammonium chloride was added and the two phases were decanted. Extraction was carried out with ethyl acetate, followed by drying and concentrating to obtain 35.12 g of product which was purified by chromatography on silica, eluting with a hexane - ethyl acetate mixture (9-1) to obtain 13.8 g of the desired product.

STEP D: Methyl 2-(4-methoxy-phenyl)-7-benzofuranacetate 10.6 ml of Triton B at 35% in methanol were introduced into a mixture of 15 g of the product of Step C, 6 ml of methyl methyl sulfinylmethyl sulfide and 25 ml of tetrahydrofuran. The solution was refluxed for 150 minutes and was poured into water and extracted with isopropyl ether. The extracts were dried and concentrated to obtain 21.95 g of product which was subjected to a methanolic hydrolysis. This product was dissolved in 200 ml of a solution prepared by adding 90.5 ml of acetyle chloride to 366 ml of methanol cooled down to 0° C. After 48 hours of stirring at ambient temperature, the solution was poured into water, and sodium bicarbonate was added. Extraction was carried out with ether and the extracts were dried and brought to dryness to obtain 16.5 g of product which was chromatographed on silica, eluting with a hexane ethyl acetate mixture (9-1) to obtain 11 g of the desired product.

| NMR CDCl$_3$ 250 MHz ppm | |
| --- | --- |
| 2 OCH$_3$ | 3.73 ppm 3.87 |
| —C$_6$H$_3$—CH$_2$—CO | 4.00 ppm |
| H$_6$ | 6.89 |
| Aromatics | 6.98 (2H) |
|  | 7.78 (2H) |
|  | 7.16 to 7.48 (3H) |

EXAMPLE 2

Methyl α-[(E)-methoxymethylene1-2-(3-methoxy-phenyl)-7-benzofuranacetate and the corresponding Z isomer Using the procedure of Example 1, methyl 2-(3-methoxy-phenyl)-7-benzofuranacetate prepared hereafter was reacted to obtain desired product melting at 110° C. and the Z isomer melting at 130° C.

PREPARATION 2

Methyl 2-(3-methoxy-phenyl)-7-benzofuranacetate

STEP A: 2-(3-methoxy-phenyl)-7-benzofurancarbaldehye

A mixture of 11 g of 2-hydroxy-3-iodo benzaldehyde, 8.6 g of (3-methoxy-phenyl) acetylene and 150 ml of pyridine was refluxed for 45 minutes and then allowed to return to ambient temperature. Ethyl acetate was added, and washing was carried out with an acid solution, followed by drying and concentrating to obtain 16 g of product which was chromatographed on silica (eluant: hexane-isopropyl ether (7-3)) to obtain 9 g of the desired product melting at 55° C. to 60° C.

STEP B: Methyl 2-(3-methoxy-phenyl)-7-benzofuranacetate

A mixture of 7.4 g of the product of Step A, 4.4 g of methyl methylsulfinyl methyl sulfide, 75 ml of tetrahydrofuran and 7 ml of Triton B was refluxed for one hour and then was poured into water and extracted with dichloromethane. The extracts were dried and concentrated to obtain.10 ml of produce which was dissolved in a 2N hydrochloric acid solution in methanol. The solution was stirred for 24 hours, treated with sodium bicarbonate, and stirred for one hour. After separating, extraction was carried out with ether and the extracts were washed and concentrated to obtain 9 g of product which was chromatographed on silica to obtain (eluant: hexane-ethyl acetate (9-1)) 4.3 g of the desired product which was used as is.

| NMR CDCl$_3$ 250 MHz ppm | |
| --- | --- |
| 2 OCH$_3$ | 3.72 (s) 3.87 (s) |
| —C$_6$H$_5$—CH$_2$—CO | 3.99 (s) |
| H'$_6$ | 6.88 (d,m) |
| H$_3$ | 7.01 (s) |
| Aromatics | 7.17 to 7.5 (7H) |

EXAMPLE 3

Methyl α-[(E)-methoxymethylene1-2-phenyl-7-benzofuranacetate and the corresponding Z isomer Using the procedure of Example 1, methyl 2-phenyl-7-benzo-furanacetate, prepared hereafter in Preparation 3, was reacted to obtain the desired E isomer melting at 126.4° C. and the Z isomer melting at 110 5° C.

PREPARATION 3

Methyl 2-phenyl-7-benzofuranacetate

STEP A: 2-phenyl-7-benzofuranacetonitrile 11 g of potassium cyanide were added to 110 ml of methanol and then 23.5 g of 7-(bromomethyl)-2-phenyl benzofuran (Helvetica Chimica Acta, Vol. 57, 5, 1974, p. 1381) in 250 ml of methanol were added. The mixture was refluxed for 5 hours, then separated, filtered and concentrated. The crystals were crystallized from flugene-1,1,3 at reflux to obtain 5.78 g of the desired product melting at 65° C.

STEP B: 2-phenyl-7-benzofuranacetic acid

A suspension of 24.68 g of the product of Step A, 200 ml of methanol, 100 ml of water and 160 ml of a ION sodium hydroxide solution was refluxed for 16 hours and the methanol was eliminated. The product was taken up in water and washed with methylene chloride. Acidification was carried out with 150 ml of a 12N hydrochloric acid solution. The product was separated out, made into a paste in water and dried to obtain 22 g of the desired product melting at 139.1° C.

STEP C: Methyl 2-phenyl-7-benzofuranacetate

A solution of 20.45 g of the product of Step B, 200 ml of methanol and 6 g of p-toluene sulfonic acid was refluxed for one hour and the solution was brought to dryness, then poured into water. Extraction was carried out with methylene chloride and the extracts were dried, filtered and concentrated to obtain 21.33 g of the desired product with a Rf =0.33 (eluant: hexane - methylene chloride (60-40)).

| NMR CDCl$_3$ 250 MHz ppm | |
|---|---|
| OCH$_3$ | 3.72 (s) |
| —C$_6$H$_5$—CH$_2$—CO | 4.00 |
| H'$_6$ | 7.02 (s) |
| H$_3$ | 7.48 |
| Aromatics | 7.2 to 7.85 (7H) |

EXAMPLE 4

Methyl α-[(E)-methoxymethylene1-2-(4-methoxy-benzoyl)-7-benzo-furanacetate and the corresponding Z isomer Using the procedure of Example 1, methyl 2-(4-methoxy-benzoyl)-7-benzofuranacetate, prepared hereafter, was reacted to obtain the desired product with a Rf 0.07 (eluant: hexane - ethyl acetate (75-25)).

PREPARATION 4

Methyl 2-(4-methoxy-benzoyl)-7-benzofuranacetate

STEP A: (4-methoxy-phenyl) (7-methyl-2-benzofuranyl)-ketone 99 ml of a normal sodium hydroxide solution were introduced at 0° C. into a solution of 13.45 g of 2-hydroxy-3-methyl benzaldehyde in methanol and the mixture was stirred at ambient temperature for 2 hours 30 minutes. After evaporation to dryness, the residue was taken up in methanol, dried and brought to dryness. The product was made into a paste in a mixture of methylene chloride-isopropyl ether and ethyl acetate. After filtration and drying had been carried out, 15.4 g of intermediate phenate were obtained which was poured into 60 ml of dioxane which had been heated to approx. 95° C. to 100° C. 20.53 g of 4'-methoxy-2-bromo acetophenone in solution in dioxane were added and the reaction medium was held at 95° C. for 4 hours, then poured into a solution of monopotassium phosphate buffer. After extraction with ethyl acetate, the extracts were dried and evaporated to dryness. The product was purified by chromatography on silica, eluting with a mixture of hexane and methylene chloride (50-50) to obtain 15.4 g of the desired product with a Rf =0.1.

STEP B: [7-bromomethyl-benzofuranl](4-methoxy-phenyl)-ketone 13.4 g of N-bromo succinimide and a small amount of azobisdiisobutyronitrile were added to a solution of 15.4 g of the product of Step A in 150 ml of carbon tetrachloride and the mixture was refluxed for 18 hours while exposed to light. It was filtered and the filtrate was brought to dryness. The product was purified by chromatography on silica, eluting with a hexane - methylene chloride mixture (50-50) to obtain the desired product with a Rf =0.08.

STEP C: Methyl 2-(4-methoxy-benzoyl)-7-benzofuranacetate 3.8 g of potassium cyanide were added to a solution of 10 g of the product of Step B in 150 ml of methanol and the mixture was refluxed for 12 hours, then poured into water. Extraction was carried out with methylene chloride and the extracts were washed with water, dried on magnesium sulfate and brought to dryness to obtain 8.48 g of product which was poured into 170 ml of methanol. 50 ml of water and 45 ml of a 10N sodium hydroxide solution were added and the mixture was refluxed for 4 hours. The methanol was evaporated off, and the mixture was poured into water and extracted with methylene chloride. The aqueous phase was acidified with concentrated hydrochloric acid and extracted with ethyl acetate. The extracts were dried and brought to dryness to obtain 7.37 g of product which was poured into 70 ml of methanol. 700 mg of p-toluene sulfonic acid were added and the mixture was refluxed for 75 minutes and then was poured into water. Extraction was carried out with methylene chloride and the extracts were washed with water and brought to dryness. The residue was taken up in 80 ml of acetone and 800 mg of p-toluene sulfonic acid, followed by stirring for 15 minutes, pouring into water, and extracting with methylene chloride. The extracts were dried and evaporated to dryness to obtain a product which was purified by chromatography on silica, eluting with a hexane - ethyl acetate mixture (8-2) to obtain 6.65 g of the desired product.

| NMR CDCl$_3$ 250 MHz ppm | |
|---|---|
| 2 OCH$_3$ | 3.74 (s) |
|  | 3.92 (s) |
| —C$_6$H$_5$—CH$_2$—CO | 4.03 (s) |
| H'$_6$ | 7.56 (s) |
| Aromatics | 7.02 to 8.15 (7H) |

Using the above procedure, the following products were prepared.

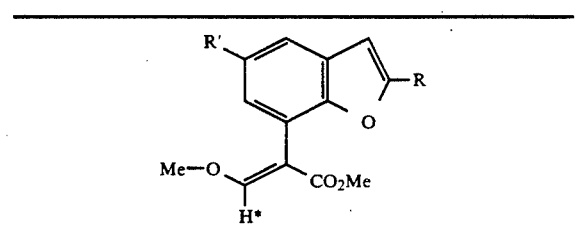

| Ex. | R | R' | E/Z | M.p. | NMR δH* ppm | Preparation |
|---|---|---|---|---|---|---|
| 1 | 4-CH$_3$O—C$_6$H$_4$ | H | E | 176° | 7.72 | 1 |
| 1 | " | H | Z | 124° | 6.96 | 1 |
| 2 | 3-CH$_3$O—C$_6$H$_4$ | H | E | 110° | 7.73 | 2 |
| 2 | " | H | Z | 130° | 6.97 | 2 |
| 3 | C$_6$H$_5$— | H | E | 126° | 7.74 | 3 |
| 3 | " | H | Z | 110° | 6.96 | 3 |
| 4 | 4-CH$_3$O—C$_6$H$_4$CO— | H | E | oil | 7.74 | 4 |
| 4 | " | H | Z | oil | 7.04 | 4 |
| 5 | C$_6$H$_5$CO— | H | E | 100-110° | 7.73 | 4 |
| 5 | " | H | Z | 140° | 7.05 | 4 |
| 6 | 2-CH$_3$O—C$_6$H$_4$—CO— | H | E | Resin | 7.69 | 4 |
| 6 | " | H | Z | Resin | 7.09 | 4 |
| 7 | 3-CH$_3$O—C$_6$H$_4$—CO— | H | E | 118° | 7.74 | 4 |
| 7 | " | H | Z | 84° | 7.07 | 4 |
| 8 | 4-Br 3-CF$_3$—C$_6$H$_3$—CO | H | E | 154° | 7.74 | 4 |
| 9 | 2-CH$_3$O—C$_6$H$_4$ | H | E | 166° | 7.73 | 2 |
| 9 | " | H | Z | oil | 6.98 | 2 |
| 10 | 2-Cl—C$_6$H$_4$ | H | E | 108° | 7.73 | 2 |
| 10 | " | H | Z | oil | 6.98 | |
| 11 | 3-Cl—C$_6$H$_4$ | H | E | oil | 7.75 | 2 |
| 11 | " | H | Z | 134° | 6.96 | 2 |
| 12 | 4-Cl—C$_6$H$_4$ | H | E | 184° | 7.73 | 2 |
| 12 | " | H | Z | 132° | 6.94 | 2 |

-continued

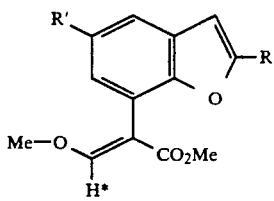

| Ex. | R | R' | E E/Z | M.p. | NMR δH* ppm | Preparation |
|---|---|---|---|---|---|---|
| 13 | C₆H₅— | I | E | 285° | 7.72 | 4 |
| 13 | " | I | Z | res. | 6.93 | 4 |

δH are expressed in ppm relative to an internal reference: tetramethylsilane. All the solutions were prepared in CDCl₃.

EXAMPLE 14

Methyl α[(E) methoxymethylene1-2-4-bromo-3-(trifluoromethyl)-phenyl]benzofuran acetate and the corresponding Z isomer 2.59 g of methyl 7-[2-[4-bromo-3-trifluoromethyl)-phenyl]benzofuranyl]acetate prepared as indicated below were added dropwise at ambient temperature to 600 mg of sodium hydride in suspension in 12 ml of dimethylformamide and 8.5 ml of methyl formate in solution in 25 ml of dimethylformamide were added. The mixture was stirred for one hour and 3.9 ml of methyl iodide were added dropwise, followed by stirring for 30 minutes. Then, the reaction medium was poured into an ice-cooled sodium phosphate solution and extraction was carried out with isopropyl ether. The extracts were dried and the solvent was eliminated under reduced pressure. The residue was chromatographed on silica (eluant: hexane ethyl acetate 85-15) to obtain 0.32 g of the desired Z isomer melting at 114° C. and 1.76 g of the desired E isomer which was made into a paste in pentane to obtain 1.63 g of E isomer melting at 134° C.

| NMR Spectrum (CDCl₃ 250 MHz ppm) | |
|---|---|
| E isomer 2-OCH₃: | 3.75 (s), 3.89 (s) |
| δH | 7.75 (s) |
| Z isomer 2-OCH₃: | 3.78 (s), 4.00 (s) |
| δH | 6.97 (s) |

PREPARATION 14

Methyl 7-2-4-bromo-3-trifluoromethyl)-phenyl-benzofuranyl-]acetate

STEP A: 4-bromo-3-trifluoromethyl iodobenzene 120 ml of concentrated hydrochloric acid Were added to 60 g of 4=bromo-3-(trifluoromethyl)- aniline suspended in 500 ml of water and the mixture was heated to 80° C., cooled down to 0° C.±5. 24.15 g of sodium nitrite in solution in 150 ml of water were added over 30 minutes and the mixture was stirred for one hour. 127.4 g of sodium iodide dissolved in 130 ml of water were added to this solution over 40 minutes and the reaction mixture was stirred for 16 hours at ambient temperature, then extracted with methylene chloride. The organic phase was washed with a 3N solution of sodium thiosulfate, then with water, and dried. Then, the solvents were eliminated under reduced pressure and after purification by chromatography on silica (eluant: hexane - ethyl acetate 6-4), 83.95 g of the expected product were obtained.

STEP B: 4-bromo-3-(trifluoromethyl)-phenylethynyl]trimethylsilane 16.7 ml of triethylamine, 11.83 ml of trimethylsilylacetylene, 325 mg of copper iodide and 600 mg of bis-(triphenylphosphine) palladium dichloride were added to 30 g of the product of Step A in solution in 90 ml of dimethylformamide. After stirring for one hour, the reaction medium was poured into ice-cooled water and the aqueous phase was extracted with isopropyl ether and dried. The solvents were eliminated and after chromatography on silica (eluant: hexane), 24.04 g of the expected product were obtained.

STEP C: 4-bromo-3-(trifluoromethyl)-phenyl acetylene 1 g of potassium carbonate was added to 24 g of the product of Step B in solution in 240 ml of methanol and after stirring for 45 minutes, the methanol was partially evaporated off. Dilution was carried out with methylene chloride and the mixture was poured into a 10% aqueous sodium bicarbonate solution. Extraction was carried out with methylene chloride and the extracts were dried. The solvent was eliminated under reduced pressure to obtain 17.73 g of the expected product melting at <50° C.

STEP D: 7-2-4-bromo-3-(trifluoromethyl)-phenyl]-benzofuranyl carboxaldehyde 7 g of the product of Step C and 6.62 g of 3-iodo-2-hydroxy benzaldehyde were added to 2.3 g of copper oxide (I) in suspension in 70 ml of pyridine and the mixture was refluxed for 90 minutes, poured into a concentrated hydrochloric acid solution, filtered, and extracted with methylene chloride. The extracts were dried and the solvent was eliminated under reduced pressure. The residue was chromatographed on silica (eluant: hexane - methylene chloride 5-5) to obtain 6 g of product which was made into a paste in pentane to obtain 4.85 g of the expected product.

STEP E: Methyl 7-[2-4-bromo-3-trifluoromethyl)-phenyl -benzo-furanyl]acetate

A solution of 4.84 g of the product of Step D, 1.65 ml of methyl methylsulfinylmethyl sulfide and 3.5 ml of triton B R at 35% in methanol was refluxed for 5 hours 30 minutes and the solution was poured into a saturated aqueous solution of sodium chloride. Extraction too place with ethyl acetate and the extracts were dried and the solvents were eliminated to obtain 7.22 g of intermediate 7-[2-[4-bromo-3-trifluoromethyl)-phenyl]-benzofuranyl]-1-(methyl-sulfinyl)-methylthio]ethylene which was dissolved in 60 ml of methanol, cooled down to 0° C. to +5° C. A methanol solution of 3.5N hydrochloric acid was added (prepared from 21 ml of acetyl chloride in 82 ml of methanol) and the mixture was stirred for 4 hours at ambient temperature. The reaction medium was poured into a 10% aqueous sodium bicarbonate solution and extracted with isopropyl ether. The extracts were dried and concentrated to dryness. The residue was chromatographed on silica (eluant: hexane methylene chloride 5-5) and after making into a paste in pentane and another chromatography, 2.65 g of the expected product were obtained.

NMR Soectrum (CDCl$_3$ 259 MHz ppm) —OCH$_3$ 3.75 (s); C$_6$H$_3$—CH$_2$—CO 4.00 (s).

EXAMPLE 15

Methylene α-[(E)-(methoxymethylene)-2-[4-chloro-(3-methoxy)-phenyl -7-benzofuranacetate and the corresponding Z isomer Using the procedure of Example 14, 3.8 g of methyl 7-[2-[4- chloro-(3-methoxy)]-phenyl]-benzofuranyl acetate prepared as below, 1.1 g of sodium hydride, 14.2 ml of methyl formate and 12.7 ml of methyl iodide were reacted to obtain 5.8 g of crude product which was chromatographed on silica (eluant: hexane - methylene chloride -acetone 90-05-05) to obtain 1.8 g of the desired E isomer melting at 131.6° C. and 0.7 g of the desired Z isomer melting at 128.1° C.

| NMR Spectrum: (CDCl$_3$ 250 MHz ppm): | |
|---|---|
| E isomer 3-OCH$_3$ | 3.74 (s) 3.88 (S) 3.98 (s) |
| δH | 7.73 (s) |
| Z isomer 3-OCH$_3$ | 3.75 (s) 3.98 (s) 3.99 (s) |
| δH | 6.94 (s) |

PREPARATION 15

Methyl 7-[2-[4-chloro-(3-methoxy)1-phenyl -benzofuranyl acetate

STEP A: [4-chloro-3-methoxyphenylethynyl -trimethylsilane

Using the procedure of Step B of Preparation 14, 5 ml of 4-chloro-3-methoxy bromobenzene, 5.2 ml of trimethylilylacetylene and 260 mg of bis-(triphenylphosphine) palladium dichloride were reacted to obtain 6.9 g of the expected product.

STEP B; 4-chloro-3-methoxyphenylacetylene

Using the procedure of Step C of Preparation 14, 8 g of the product of Step A and 0.46 g of potassium carbonate were reacted to obtain 5.2 g of the expected product.

STEP C: Formyl 7-[2-[4-chloro-(3-methoxy)-phenyl)-benzofuranyl

Using the procedure of Step D of Preparation 14, 5.2 g of the product of Step B, 7.3 g of 3-iodo-2-hydroxy benzaldehyde in the presence of 2.5 g of copper oxide in 75 ml of pyridine were reacted to obtain 9.8 g of the expected product.

STEP D: Methyl 7-2-4-chloro-(3-methoxy)1-phenyl -benzofuranyl acetate

Using the procedure of Step E of Preparation 14, 7.5 g of the product of Step C, 4 ml of methyl methylsulfinylmethyl sulfide and 4.7 ml of Triton B ® at 35% in methanol were reacted to obtain 8 g of the intermediate which was treated with a methanol solution of hydrochloric acid. After chromatography on silica (eluant: hexane - ethyl acetate 9-1), 4.7 g of the expected product melting at 97.7° C. were obtained.

NMR Spectrum (CDCl$_3$ 250 MHz ppm): 2—OCH$_3$ 4.00 (s,5H) 3.73 (s,3H)

EXAMPLE 16

Methyl α-(E)methoxymethylene1-7-[2-[4-(2-isopropyl-thiazolyl)-benzofuranyl]-acetate 540 mg of methyl 7-[2-[4-(2-isopropyl)-thiazolyl]-benzofuranyl]acetate prepared as below in 4 ml of dimethylformamide and 1.7 ml of methyl formate was added over 20 minutes to 170 mg of sodium hydride in 2 ml of dimethylformamide and the mixture stood for 3 hours at ambient temperature. 0.2 ml of methyl iodide were added and the mixture was stirred for one hour, followed by extraction with isopropyl ether. The extracts were washed with water, dried and concentrated. The residue was chromatographed on silica (eluant: hexane - isopropyl ether 7-3 then 8-2) to obtain 240 mg of the expected product.

| NMR Spectrum (CDCl$_3$ ppm): | |
|---|---|
| 2-OCH$_3$-0 | 3.72 (s) 3:87 (s) |
| δH | 7.71 (s) |

PREPARATION 16

Methyl 7-[2-[4-(2-isopropyl)-thiazolyl-benzofuranyl]acetate

STEP A: Methyl 2-hydroxy-3-carbonyl phenyl acetate 24 g of 2-hydroxy phenyl acetic acid in 50 ml of water were heated to 120° C. in the presence of 50 g of sodium hyroxide and 100 ml of chloroform were added over 3 hours, followed by cooling and extraction with 500 ml of chloroform and 500 ml of water. After decanting, the chloroform solution was eliminated and the aqueous phase was acidified with concentrated hydrochloric acid and extracted with chloroform. The extracts were concentrated under reduced pressure to obtain 6 g of intermediate aldehyde to which 30 ml of a methanol solution of hydrochloric acid were added, followed by concentrating under reduced pressure. The residue was chromatographed on silica (eluant: hexane - ethyl acetate 85-15) to obtain 2.9 g of the expected product melting at <50° C.

STEP B: Methyl 7-(2-acetylbenzofuranyl) acetate 5.5 g of the product of Step A in 40 ml of dioxane and 3.8 ml of chloroacetone in the presence of 5.9 g of potassium carbonate were refluxed for 15 minutes and the mixture was filtered and concentrated under reduced pressure. After chromatographing the residue on silica (eluant: hexane - ethyl acetate 8-2), 4 g of the expected product melting at 80° C. were obtained.

STEP C: Methyl 7-(2-bromoacetyl) benzofuranyl acetate 2.97 ml of a molar solution of 1,8-diazabicyclo[5.4.0]-undec -7-ene in methylene chloride and a molar solution of trimethylsilyl bromide in methylene chloride were added under inert atmosphere to 530 mg of the product of Step B and the mixture was stirred for 6 hours at reflux. 0.5 ml of each of the 2 solutions were added and the reaction medium was cooled down to −60° C. 2.26 ml of a molar solution of bromine in methylene chloride were added and the mixture was stirred for 15 minutes at −60° C., followed by concentrating under reduced pressure. The residue was chromatographed on silica (eluant: ethyl acetate - hexane 3-7) to obtain 530 mg of the expected product melting at 95° C.

STEP D: Methyl 7-2-[4-(2-isopropyl)-thiazolyl-benzo-furanyl]acetate 850 mg of the product of Step C and 310 mg of isopropyl thioamide in 25 ml of methanol were refluxed for 45 minutes and the mixture was concentrated under reduced pressure. The residue was taken up in 30 ml of ethyl acetate and 10 ml of aqueous saturated solution of sodium bicarbonate. After drying, and concentrating again, the residue was chromatographed on silica (eluant: hexane-ethyl acetate 9-1) to obtain 590 mg of the expected product melting at 60° C.

EXAMPLE 17

Methyl α[(E)-methoxymethylene1-2-(3,4-methylenedioxy)-phenyl-7-benzofuran acetate and the corresponding Z isomer Using the procedure of Example 1, 3.34 g of methyl 7-[2-(3,4-methylenedioxyphenyl)-benzofuranyl acetate prepared as below, 1.05 g of sodium hydride, 15 ml of methyl formate and 6.9 ml of iodomethane were reacted to obtain 6.92 g of crude product which was chromatographed on silica (eluant: hexane - methylene chloride acetone 90–0.5–0.5) to obtain 1.66 g of the desired E isomer melting at 154° C. and 0.320 g of the desired Z isomer melting at 189.7° C.

| NMR Spectrum (CDCl$_3$ 250 MHz ppm): | |
|---|---|
| E isomer 2-OCH$_3$ | 3.73 (s) 3.87 (s) |
| δH | 7.72 (s) |
| Z isomer 2-OCH$_3$ | 3.76 (s) 3.98 (s) |
| δH | 6.95 (s) |

PREPARATION 17

Methyl 7-2-(3.4-methylenedioxyphenyl)-benzofuranyl acetate

STEP A: 3,4-methylenedioxy-[1,1-dibromovinyl]-benzene 41.2 g of dibromo methyl triphenyl phosphonium bromide and then 30 ml of dimethylformamide were added to 8.98 g of potassium terbutylate in 90 ml of tetrahydrofuran and the suspension was stirred for one hour at 20° C. and cooled down to 0° C. Then, 12 g of piperonal in 20 ml of tetrahydrofuran were added slowly and the reaction medium returned to ambient temperature and was then stirred for 3 hours. The mixture was poured into an aqueous solution of sodium bisulfate and extracted with ethyl acetate. The extracts were dried and concentrated under reduced pressure to obtain 15.97 g of the expected product.

STEP B: 3.4-methylenedioxy phenyl acetylene 73 ml of 1.6M n-butyllithium in hexane were added slowly at −65° C. to 15.96 g of the product of Step A in solution in 150 ml of tetrahydrofuran. The mixture was stirred for 2 hours at −65° C. and then was poured into a saturated aqueous solution of sodium acid phosphate. The organic phase was separated out by decanting, dried and concentrated under reduced pressure to obtain 7.6 g of the expected product.

STEP C: 7-[2-(3,4-methylenedioxy)-phenyl]-benzofuranyl carboxaldehyde

Using the procedure of Step D of Preparation 14, 5 g of the product of Step B, 2.66 g of copper oxide in 60 ml of pyridine and 8.02 g of 2-hydroxy-3-iodo benzaldehyde were reacted to obtain 3.55 g of the expected product melting at 159.7° C.

STEP D: Methyl 7-2-(3,4-methylenedioxvphenyl) benzofuranyl acetate

Using the procedure of Step E of Preparation 14, 4.5 g of the product of Step C, 3.1 g of Triton B ®, and 2.72 ml of methyl methylsulfinylmethyl sulfide were reacted to obtain 7.5 g of the intermediate 1-methylsulfinyl-1-methylthio-2-(3,4-methylene-dioxyphenyl)-benzofuranyl ethylene which was treated with a methanol solution of hydrochloric acid to obtain 3.46 g of the expected product melting at 66.4° C.

| NMR Spectrum (CDCl$_3$ 250 MHz ppm): | |
|---|---|
| OCH$_3$-0 | 3.73 (s) |
| C$_6$H$_5$—CH$_2$—CO | 3.98 (s) |

EXAMPLE 18

Methyl α[(E)-methoxymethylene1-2-butyl-7-benzofuran acetate and the corresponding Z isomer Using the procedure of Example 14, 3.2 g of methyl 7-[2butyl]-benzofuranyl acetate prepared as below, 1.25 g of sodium hydride, 17.6 ml of methyl formate and 8.2 ml of iodomethane were reacted to obtain 7.56 g of crude product which was chromatographed on silica (eluant: hexane - methylene chloride - acetone 90-0.5-0.5) to obtain 1.83 g of the desired E isomer and 0.350 g of the desired Z isomer melting at 54.3° C.

| NMR Spectrum (CDCl$_3$ 250 MHz ppm): | |
|---|---|
| E isomer 2-OCH$_3$ | 3.71 (s) 3.85 (s) |
| δH | 7.67 (s) |
| Z isomer 2-OCH$_3$ | 3.74 (s) 3.95 (s) |
| δH | 6.91 (s) |

PREPARATION 18

Methyl 7-(2-butyl)-benzofuranylacetate

STEP A: 7-(2-butyl) benzofuranyl carboxaldehyde

Using the procedure of Step D of Preparation 14, 3.9 ml of 1hexane, 2.66 g of copper (I) oxide in 60 ml of pyridine and 8.02 g of 2-hydroxy-3-iodo-benzaldehyde were reacted to obtain 5.08 g of the expected product.

STEP B: Methyl 7-(2-butyl) benzofuranyl acetate

Using the procedure of Step E of Preparation 14, 4.72 g of the product of Step A, 4.1 g of Triton B ® and 3.6 ml of methyl methyl-sulfinylmethyl sulfide were reacted to obtain 7.0 g of the intermediate.1-methylsulfinyl-1-methylthio-2-butyl benzofuranylethylene which was treated with a methanol solution of hydrochloric acid to obtain 5.29 g of crude product which was chromatographed on silica (eluant: hexane - methylene chloride 8-2) to obtain 3.22 g of the expected product.

| NMR Spectrum (CDCl₃ 250 MHz ppm): | |
|---|---|
| OCH₃— | 3.71 (s) |
| C₆H₅—CH₂—CO | 3.92 (s) |

EXAMPLE 19

Methyl α[(E)-methoxymethylene]-2-[2-[4-(trifluoromethyxy)-pehny]-4-thiazolyl]-7-benzofuran acette and the corresponding Z isomer Using the procedure of Example 14, 0.6 g of methyl-7-[2-]4-(trifluoromethoxyphenyl)-thiazolyl]-benzofuranyl]acetate, 0.16 g of sodium hydride, 3 ml of methyl formate and 1 ml of 3 methyl iodide were reacted to obtain 0.7 g of crude product which were chromatographed on silica (eluant: heptane - ethyl acetate 8-2) to obtain 0.34 g of the desired E isomer and 0.12 g of the desired Z isomer. After trituring the E isomer in hexane, 0.27 g of product melting a 132° C. were obtained.

| NMR Spectrum (CDCl₃ 250 MHz ppm) | |
|---|---|
| E isomer 2-OCH₃ | 3.75 (s) 3.89 (s) |
| δH | 7.74 (s) |

PREPARATION 19

Methyl 7-2-[4-(trifluoromethyoxyphenyl)-thiazolyl]-benzofuranyl]acetate

Using the procedure of Step D of Preparation 16, methyl 7-(2bromoacetyl) benzofuranyl acetate and trifluoromethoxythioamide were reacted to obtain the desired product.

Using the procedure of the previous examples and starting with the apporprite compounds, the products of Examples 20 to 44 were prepared.

EXAMPLE 20: (RS) methyl 2-[hydroxy-(3-methoxyphenylmethyl)]-alpha-(methoxymethylene)-7-benzofuran acetate.

EXAMPLE 21: (RS) methyl 2-[hydroxy-(4-methoxyphenylmethyl]-alpha-(methoxymethylene)-7-benzofuran acetate.

EXAMPLE 22: Methyl α-[(E)-methoxymethylene]-2-[[(E)-hydroxyimino]-phenylmethyl)]-7-benzofuran acetate.

EXAMPLE 23: Methyl α-[(E)-methoxymethylene]-2-[[(Z)-hydroxyimino]-phenylmethyl)]-7-benzofuran acetate.

EXAMPLE 24: Methyl α-[(E)-methoxymethylene]-2-(3-phenoxyphenyl)-7-benzofuran acetate and the corresponding Z isomer.

EXAMPLE 25: Methyl α-[(E)-methoxymethylene]-2-(4-phenoxyphenyl)-7-benzofuran acetate and the corresponding Z isomer.

EXAMPLE 26: Methyl α-[(E)-methoxymethylene]-2-[4-(2-phenyl)thiazolyl]-7-benzofuran acetate and the corresponding Z isomer.

EXAMPLE 27: Methyl α-[(E)-methoxymethylene]-2-[2-chloro-4,5methylenedioxy]-phenyl]-7-benzofuran acetate and the corresponding Z isomer.

EXAMPLE 28: Methyl α-[(E)-methoxymethylene]-2-[4-(2-trifluoro-methyl-thiazolyl]-7-benzofuran acetat EXAMPLE 29: Methyl α-[(E)-methoxymethylene]-2-(4-biphenylyl)-7benzofuran acetate.

EXAMPLE 30: Methyl α-[(E)-methoxymethylene]-2-(3-biphenylyl)-7benzofuran acetate.

EXAMPLE 3I: Methyl α-[(E)-methoxymethylene]-2-(1-naphthyl)-7benzofuran acetate.

EXAMPLE 32: Methyl α-[(E)-methoxymethylene]-2-(2-naphthyl)-7benzofuran acetate.

EXAMPLE33:Methylo-[(E)-methylthiomethylene]-2-(4-methoxyphenyl)7-benzofuran acetate.

EXAMPLE 34: Methyl α-[(E)-methoxymethylene]-2-(4-nitrophenyl)-7-benzofuran acetate and the corresponding Z isomer.

EXAMPLE 35: Methyl α-[(E)-methoxymethylene]-2-(2-methylthio -4-thiazolyl)-7-benzofuran acetate and the corresponding Z isomer.

EXAMPLE 36: Methyl α-[(E)-methoxymethylene]-2-(2-diethylamino -4-thiazolyl)-7-benzofuran acetate and t EXAMPLE 37: Methyl α-[(E)-methoxymethylene]-2-trifluoromethyl-7benzofuran acetate and the corresponding Z isomer.

EXAMPLE 38: Methyl α-[(E)-methoxymethylene]-2-heptafluoropropyl -7-benzofuran acetate and the corresponding Z isomer.

EXAMPLE 39: Methyl α-[(E)-methoxymethylene]-2-cyclohexyl-7benzofuran acetate and the corresponding Z isomer.

EXAMPLE 40: Methyl α-[(E)-methoxymethylene]-2-isopropyl-7benzofuran acetate and the corresponding Z isomer.

EXAMPLE 41: Methyl α-[(E)-methoxymethylene]-2-tertbutyl-7benzofuran acetate and the corresponding Z isomer.

EXAMPLE 42: Methyl α-[(E)-methoxymethylene]-2-sec-butyl-7benzofuran acetate and the corresponding Z isomer.

EXAMPLE 43: Methyl α-[(E)-methoxymethylene]-2-(3,3-dimethyl -1-butynyl)-7-benzofuran acetate and the c EXAMPLE 44:Methyl α-[(E)-methoxymethylene]-2-(2-chloroethenyl) -7-benzofuran acetate and the corresponding Z isomer.

In this way the following products were prepared using the detailed operating methods described above.

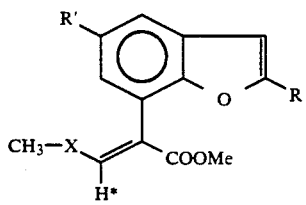

| Ex. | R' | X | E/Z | Mp °C. | NMR δH* ppm |
|---|---|---|---|---|---|
| 14 | 4-Br 3-CF$_3$—C$_6$H$_3$ | H O | E | 134 | 7.75 |
|  |  | H O | Z | 114 | 6.94 |
| 15 | 4-Cl 3-CH$_3$O—C$_6$H$_3$— | H O | E | 131 6 | 7.73 |
|  |  | H O | Z | 128 1 | 6.94 |
| 16 | 4-[2-(CH$_3$)$_2$CH—C$_3$HNS]— | H O | E | oil | 7.71 |
| 17 | 3,4(—O—CH$_2$—O)C$_6$H$_3$— | H O | E | 154 | 7.72 |
|  |  | H O | Z | 189.7 | 6.95 |
| 18 | n-C$_4$H$_9$— | H O | E | oil | 7.67 |
|  |  | H O | Z | 54.3 | 6.91 |
| 19 | 4-[2-[4-CF$_3$O—C$_6$H$_4$C$_3$HNS— | H O | E | 132 | 7.74 |
| 20 | 3-CH$_3$O—C$_6$H$_4$—CHOH— | H O | E | resin | 7.62 |
| 21 | 4-CH$_3$O—C$_6$H$_4$—CHOH— | H O | E | oil | 7.63 |
| 22 | C$_6$H$_5$—C=NOH— (E) | H O | E | resin | 7.68 |
| 23 | C$_6$H$_5$—C=NOH— (Z) | H O | E | 124 | 7.64 |
| 24 | 3-C$_6$H$_5$—OC$_6$H$_4$— | H O | E | 132.4 | 7.69 |
|  |  | H O | Z | resin | 7.00 |
| 25 | 4-C$_6$H$_5$—OC$_6$H$_4$— | H O | E | 149.9 | 7.72 |
|  |  | H O | Z | 152.8 | 6.96 |
| 26 | 4-(2-C$_6$H$_5$—C$_3$HNS)— | H O | E | 165 | 7.59 |
|  |  | H O | Z | oil | 6.95 |
| 27 | 2-Cl 3,4(—OCH$_2$—O)C$_6$H$_3$— | H O | E | 150.5 | 7.73 |
|  |  | H O | Z | 237.3 | 6.96 |
| 28 | 4-[2-CF$_3$—C$_3$HNS]— | H O | E | 95 | 7.73 |
| 29 | 4-C$_6$H$_5$—C$_6$H$_4$— | H O | E | 223.3 | 7.75 |
| 30 | 3-C$_6$H$_5$—C$_6$H$_4$— | H O | E | 102 | 7.74 |
| 31 | 1-C$_{10}$H$_7$ | H O | E | 132.2 | 7.73 |
| 32 | 2-C$_{10}$H$_7$ | H O | E |  |  |
| 33 | 4-CH3O—C$_6$H$_4$ | H S | E | 137-138 | 8.02 |
| 34 | 4-NO2—C$_6$H$_4$— | H O | E | — | 7.75 |
|  |  |  | Z | — | — |
| 35 | 4-[2-CH$_3$S—C$_3$HNS]— | H O | E | — | 7.72 |
|  |  |  | Z | — | — |
| 36 | 4-[2-(C$_2$H$_5$)$_2$N—C$_3$HNS]— | H O | E | — | 7.74 |
|  |  |  | Z | — | — |
| 37 | —CF$_3$— | H O | E | oil | 7.81 |
|  |  |  | Z | — | — |
| 38 | —CF$_2$—CF$_2$—CF$_3$ | H O | E | oil | 7.82 |
|  |  |  | Z | — | — |
| 39 | —C$_6$H$_{11}$ | H O | E | resin | 7.70 |
|  |  |  | Z | — | — |
| 40 | —CH—(CH$_3$)$_2$ | H O | E | oil | 7.71 |
|  |  |  | Z | — | — |
| 41 | —C—(CH$_3$)$_3$ | H O | E | resin | 7.74 |
|  |  |  | Z | — | — |
| 42 | —(CH$_3$)CH—C$_2$H$_5$ | H O | E | oil | 7.73 |
|  |  |  | Z | — | — |
| 43 | —C≡C—(CH$_3$)$_3$ | H O | E | oil | 7.69 |
|  |  |  | Z | — | — |
| 44 | —C=CH—Cl | H O | E | resin | 7.81 |
|  |  |  | Z | — | — |

EXAMPLE 45: Preparation of a Soluble Concentrate

A soluble concentrate were prepared containing as active ingredient the product of Example 1 (E).

EXAMPLE 46: Preparation of an Emulsifiable Concentrate

An emulsifiable concentrate was prepared containing as active ingredient the product of Example 11 (E).

BIOLOGICAL ACTIVITY

I—Funoicide activity

Tests on *Plasmopara viticola*

Young vine plants from cuttings (Grenache N variety, clone 70) were cultivated in a greenhouse (daytime temperature: 30° C., night-time temperature: 25° C.) on an earth/compost/sand mixture, (1/3-1/3-1/3). Two days before the test, the plants were moved into a culture chamber with the same temperature conditions and humidity 60% in the day, 80% at night. The product was dissolved in "matrix A" at a concentration of 100 ppm just before use. The treatment took place by spraying the solution on the leaves until saturation Contamination was carried out with a suspension of zoospores of Plasmopara viticola taken immediately before the test using 50,000 zoospores per ml. Drops of suspension (20 micro-liters) were deposited on the abaxial surface of the leaves. The plants were then kept for 24 hours in an atmosphere saturated with water-vapour. Then, the atmosphere was returned to the humidity of the culture chamber (60% in the day, 80% at night). The reading was taken ten days after contamination by measuring the development of clusters of sporangiophores on the abaxial surface of the leaves. The effectiveness of the product was calculated relative to a non-treated control. The same type of test was carried out on a Chardonnay vine.

The results obtained in % of effectiveness on plasmopara viticola at 100 ppm of active material were as follows:

| Product | Grenache vine | Chardonnay vine |
|---|---|---|
| Ex. No 1 (E) | 90 | n. d. |
| Ex. No 1 (Z) | 100 | n. d. |
| Ex. No 2 (E) | 100 | 100 |
| Ex. No 10 (E) | 100 | 90 |
| Ex. No 11 (E) | 100 | 100 |
| Ex. No 12 (E) | 100 | 100 | n. d. = not determined

Example of composition of "MATRIX A":

| Solvesso 150 | 70.0 g |
|---|---|
| NAPSOL PM1 | 850.0 g |
| SURFAROX HRH 40 c | 52.0 g |
| ECD 1604 | 28.0 g |
| | 1000.0 g |

II —Insecticide activity a) Effect on *Spodoptera Littoralis (S.L.)* Larvae by Contact and Ingestion.

L3 stage *SPODOPTERA LITTORALIS* larvae were used and the operation was carried out at 22° C. at relative humidity conditions of 50%. Petri dishes were used containing a damp circular piece of filter paper and in each dish, two bean plant leaves were placed and treated with hydroacetonic solution (50-50) containing the product under test. The dead larvae were counted at the end of 7 days and the concentration $LC_{50}$ were expressed in ppm.

b) Study of the lethal Effect on *Musca Domestica (M.D.)*:

6-day-old female flies weighing 18 to 20 mg were used and the operation was carried out at 22° C. at relative humidity conditions of 50%. The products were administered by topical application of an acetone solution of 1 g/l on the dorsal thorax of the insects. The $LC_{50}$ dose was determined and was expressed in ppm.

C) Study of the Activity on *Aphis Cracivora*:

2 ml of water acetone solution (50/50) was sprayed on broad bean leaves (vicia fabae) until the leaves were running with solution. After drying, 15 female apter of *Aphis cracivora* were deposited on the leaves and the mixture was kept on the damp filter paper inside a Petri dish. 24 hours after the start of contact, the number of dead insects was determined and the $LC_{50}$ dose expressed in ppm were determined.

III—Acaricide Study of the Compounds of the Invention

Bean plants were used comprising 2 leaves infested with 30 females of *Tetranychus Urticae* per leaf and put under an aerated hood under a lighted ceiling which was constantly on. The plants were treated with a Fisher gun with 4 ml of toxic solution per plant of a mixture with an equal volume of water and acetone. After leaving to dry for half an hour the infestation was proceeded with and mortality checks were carried out at the end of 3 days. The $LC_{50}$ dose was determined and the results are set out in the table below, taking account of the following values:

| A: | $LC_{50} < 250$ ppm |
|---|---|
| B: | $250 \leq LC_{50} \leq 1000$ ppm |
| C: | $LC_{50} > 1000$ ppm |

| Product of Example | Fly | Spodoptera | Aphis | Tetranychus |
|---|---|---|---|---|
| 3 (E) | — | B | — | — |
| 3 (Z) | — | B | — | — |
| 1 (E) | — | B | — | A |
| 12 (E) | A | — | — | A |
| 11 (E) | — | B | — | — |
| 1 (Z) | — | B | — | A |
| 14 (E) | A | B | — | A |
| 24 (E) | A | — | — | — |
| 25 (E) | A | — | — | — |
| 17 (E) | A | A | — | — |
| 15 (E) | A | B | A | B |
| 19 (E) | — | A | — | — |
| 18 (E) | — | — | A | A |
| 16 (E) | — | — | — | A |

Various modifications of the compounds and method of the invention may be made without departing from the spirit or scope thereof and it is to be understood that the invention is intended to be limited only as defined in the appended claims.

We claim:
1. A compound of the formula

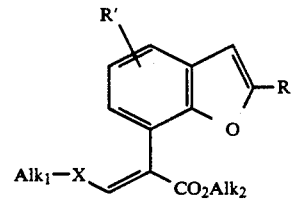

wherein R is selected from the group consisting of hydrogen, optionally substituted alkyl, alkenyl and alkynyl of up to 8 carbon atoms, optionally substituted cycloalkyl or cycloalkenyl of up to 8 carbon atoms, optionally substituted aryl of 6 to 18 carbon atoms, optionally substituted benzoyl and optionally substituted optionally substituted benzoyl and optionally substituted heterocycle, the optional aryl, aralkyl, benzoyl and heterocycle substituents being at least one member of the group consisting of halogen, thiazolyl, alkyl and alkoxy of 1 to 6 carbon atoms haloalky, —CN,—$NO_2$, aldoxycarbonyl,—$CONH_2$, —$OCF_3$, optionally substituted alkylamino or dialkylamino of 1 to 4 or carbons, —OR", —SR" in which R" is alkyl or alkenyl of 1 to 6 carbon atoms, or heterocyclo, or said optional substituent is alkylenedioxy, Alk₁ and Alk₂ are individually optionally substituted alkyl of 1 to 8 carbon atoms, X is —O— or —S— and R' is hydrogen or halogen in any position on the phenyl and the geometry of the double bond is E or Z or a mixture of E and Z the optional alkyl, alkenyl, alkynyl, cycloalkyl and cycloalkenyl substituent being at least one halogen.

2. A compound of claim 1 wherein X is —O—.

3. A compound of claim 1 wherein R' is hydrogen.

4. A compound of claim 1 wherein Alk₁ and Alk₂ are methyl.

5. A compound of claim 1 wherein R is alkyl of 1 to 8 carbon atoms.

6. A compound of claim 1 wherein R is n-butyl.

7. A compound of claim 1 wherein R is phenyl optionally substituted with at least one member of the group consisting of halogen, phenoxy, thiazolyl, alkoxy of 1 to 6 carbon atoms and alkyl substituted by at least one halogen or R is phenyl substituted on two adjacent carbons with alkylenedioxy.

8. A compound of claim 7 wherein R is phenyl substituted by alkoxy of 1 to 4 carbon atoms, halogen or both.

9. A compound of claim 7 wherein R is methoxyphenyl.

10. A compound of claim 7 wherein R is chlorophenyl.

11. A compound of claim 7 wherein R is bromophenyl.

12. A compound of claim 7 wherein R is trifluoromethylphenyl.

13. A compound of claim 7 wherein R is 3,4-methylenedioxyphenyl.

14. A compound of claim 1 wherein R is thiazolyl optionally substituted with alkyl of 1 to 8 carbon atoms or an optionally substituted phenyl.

15. A compound of claim 1 wherein R is thiazolyl substituted with isopropyl.

16. A compound of claim 1 wherein R is thiazolyl, substituted with CF₃.

17. A compound of claim 1 wherein the enol ether double bond has E geometry.

18. A compound of claim 1 selected, from the group consisting of
methyl α-[(E)-methoxymethylene]-2-(4-methoxyphenyl)-7-benzofuran acetate,
methyl α-[(E)-methoxymethylene]-2-(3-methoxyphenyl)-7-benzofuran acetate,
methyl α-[(E)-methoxymethylene]-2-(3-chlorophenyl)-7-benzofuran acetate,
methyl α-[(E)-methoxymethylene]-2-(2-chlorophenyl)-7-benzofuran acetate,
methyl α-[(E)-methoxymethylene]-2-[4-bromo-3-(trifluoromethyl)phenyl]-benzofuran acetate,
methyl α-[(E)-(methoxymethylene)-2-[4-chloro-(3-methoxy)-phenyl]-7-benzofuran acetate,
methyl α-[(E)-methoxymethylene]-7-[2-[4-(2-isopropylthiazolyl)benzofuranyl]-acetate,
methyl α-[(E)-methoxymethylene]-2-(3,4-methylenedioxy)-phenyl-7- c>benzofuran acetate,
hoxymethylene]-2-butyl-7-benzofuranacetate,
methyl α-[(E)-met
methyl α-[(E)-methoxymethylene]-2-[2-[4-(trifluoromethoxy)-phenyl]4-thiazolyl]-7-benzofuran acetate and methyl o-[(E)-methoxymethylene]-2-[4-(2-trifluoro-methyl-thiazolyl) -7-benzofuran acetate.

19. An insecticidal composition comprising an insecticidally effective amount of at least one compound of claim 1 and an inert carrier.

20. A composition of claim 19 wherein the active compound is selected from the group consisting of
methyl α-[(E)-methoxymethylene]-2-(4-methoxyphenyl)-7-benzofuran acetate,
methyl α-[(E)-methoxymethylene]-2-(3-methoxyphenyl)-7-benzofuran acetate,
methyl α-[(E)-methoxymethylene]-2-(3-chlorophenyl)-7-benzofuranacetate,
methyl α-[(E)-methoxymethylene]-2-(2-chlorophenyl)-7-benzofuran acetate,
methyl α-[(E)-methoxymethylene]-2-[4-bromo-3-(trifluoromethyl)phenyl]-7-benzofuran acetate,
methyl α-[(E)-(methoxymethylene)-2-[4-chloro-(3-methoxy)-phenyl]-7-benzofuran acetate,
methyl α-[(E)-methoxymethylene]-7-[2-[4-(2-isopropylthiazolyl)benzofuranyl]-acetate,
methyl α-[(E)-methoxymethylene]-2-(3,4-methylenedioxy)-phenyl-7benzofuran acetate,
methyl α-[(E)-methoxymethylene]-2-butyl-7-benzofuranacetate,
methyl α-[(E)-methoxymethylene]-2-[2-[4-(trifluoromethoxy)-phenyl]-4-thiazolyl]-7-benzofuran acetate and
methyl α-[(E)-methoxymethylene]-2-[4-(2-trifluoromethyl-thiazolyl) -7-benzofuran acetate.

21. A method of combatting insects comprising contacting insects with an insecticidally effective amount of at least one compound of claim 1.

22. A method of combatting acariens comprising contacting acariens with an acaricidally effective amount of at least one compound of claim 1.

23. A method of combatting fungi comprising contacting fungi with a fungicidally effective amount of at least one compound of claim 1.

* * * * *